United States Patent
Young et al.

(10) Patent No.: US 7,561,975 B2
(45) Date of Patent: Jul. 14, 2009

(54) SYSTEM, METHOD, AND COMPUTER PROGRAM PRODUCT FOR ANALYZING SPECTROMETRY DATA TO IDENTIFY AND QUANTIFY INDIVIDUAL COMPONENTS IN A SAMPLE

(75) Inventors: Sidney Stanley Young, Raleigh, NC (US); Thomas Henry Barrett, Jr., Raleigh, NC (US); Christopher William Beecher, Chapel Hill, NC (US)

(73) Assignee: Metabolon, Inc., Durham, NC (US)

( * ) Notice: Subject to any disclaimer, the term of this patent is extended or adjusted under 35 U.S.C. 154(b) by 237 days.

(21) Appl. No.: 11/688,526

(22) Filed: Mar. 20, 2007

(65) Prior Publication Data

US 2007/0288174 A1 Dec. 13, 2007

Related U.S. Application Data

(60) Provisional application No. 60/784,296, filed on Mar. 21, 2006.

(51) Int. Cl.
*G01N 31/00* (2006.01)
(52) U.S. Cl. ......................................................... 702/22
(58) Field of Classification Search ................... 702/22, 702/28, 32, 66–68, 76, 189, 196; 250/306, 250/307
See application file for complete search history.

(56) References Cited

U.S. PATENT DOCUMENTS

| | | | |
|---|---|---|---|
| 6,584,413 B1 * | 6/2003 | Keenan et al. ................. 702/28 |
| 6,675,106 B1 * | 1/2004 | Keenan et al. ................. 702/28 |
| 6,940,065 B2 * | 9/2005 | Graber et al. ................ 250/282 |
| 7,005,255 B2 | 2/2006 | Kaddurah-Daouk et al. |
| 7,016,219 B1 | 3/2006 | Davies, Jr. |
| 7,279,679 B2 * | 10/2007 | Old et al. .................... 250/282 |
| 2002/0138210 A1 * | 9/2002 | Wilkes et al. ................. 702/28 |
| 2004/0181351 A1 * | 9/2004 | Thompson et al. ............ 702/76 |
| 2006/0217911 A1 * | 9/2006 | Wang .......................... 702/85 |
| 2007/0032969 A1 | 2/2007 | Barrett, Jr. et al. |
| 2007/0250274 A1 * | 10/2007 | Volkov et al. ................. 702/22 |

OTHER PUBLICATIONS

Brunet, J-P., et al., "Metagenes and Molecular Pattern Discovery Using Matrix Factorization", *PNAS*, vol. 101, No. 12, Mar. 23, 2004, pp. 4164-4169.

(Continued)

*Primary Examiner*—Michael P. Nghiem
*Assistant Examiner*—Cindy H Khuu
(74) *Attorney, Agent, or Firm*—Alston & Bird LLP

(57) ABSTRACT

A system is provided for analyzing metabolomics data received from an analytical device across a group of samples. The system automatically receives a data matrix corresponding to each of the samples, wherein the data matrix includes rows corresponding to each of the samples and columns corresponding to a group of ions present in the respective samples. A processor is provided for determining a characteristic value corresponding to at least one of a group of components present in the samples, wherein the components are made up of at least a portion of the group of ions, using at least one of a correlation function and a factorization function. A user interface is in communication with the processor for displaying a visual indication of the characteristic value such that a user may receive a visual indication of the types of components present in the samples.

19 Claims, 7 Drawing Sheets

OTHER PUBLICATIONS

Good, I.J., "Some Applications of the Singular Decomposition of a Matrix", *Technometrics*, vol. 11, No. 4, Nov. 1969, pp. 823-831.

Hoyer, P.O., "Non-Negative Matrix Factorization with Sparseness Constraints", *Journal of Machine Learning Research*, 2004, pp. 1457-1469.

Juvela, M., et al., "The Use of Positive Matrix Factorization in the Analysisof Molecular Line Spectra from the Thumbprint Nebula", *Clouds, Cores, and Low Mass Stars*, ASP Conference Series, vol. 65, 1994, pp. 176-181, D.P. Clemens, and R. Barvainis, eds.

Lee, D.D., et al., "Learning the Parts of Objects by Non-Negative Matrix Factorization", *Nature*, vol. 401, Oct. 21, 1999, pp. 788-791.

Lee, D.D., et al., "Algorithms for Non-Negative Matrix Factorization", *Advances in Neural Information Processing Systems*, vol. 13, 2001, pp. 556-562.

Liu, L., et al., "Robust Singular Value Decomposition Analysis of Microarray Data", *PNAS*, vol. 11, No. 23, Nov. 11, 2003, pp. 13167-13172.

Nadler, B., et al., "Partial Least Squares, Beer's Law and the Net Analyte Signal: Statistical Modeling and Analysis", *Journal of Chemometrics*, vol. 19, 2005, pp. 45-54.

Sajda, P., et al., "Recovery of Constituent Spectra Using Non-Negative Matrix Factorization", $4^{th}$ *International Symposium on Independent Component Analysis and Blind Signal Separation*, (ICA2003), Apr. 2003, Nara, Japan.

Scholz, M., et al., "Metabolite Fingerprinting: Detecting Biological Features byIndependent Component Analysis", *Bioinformatics Advance Access*, vol. 20, No. 15, 2004, pp. 2447-2454.

Skillicorn, D.B., et al., "Handbook of Data Mining Using Matrix Decompositions", School of Computing, Queen's University, Kingston, Canada, Aug. 2003.

Tropp, J.A., "Literature Survey: Non-Negative Matrix Factorization", Literature Survey Report, the University of Texas at Austin, 2003.

\* cited by examiner

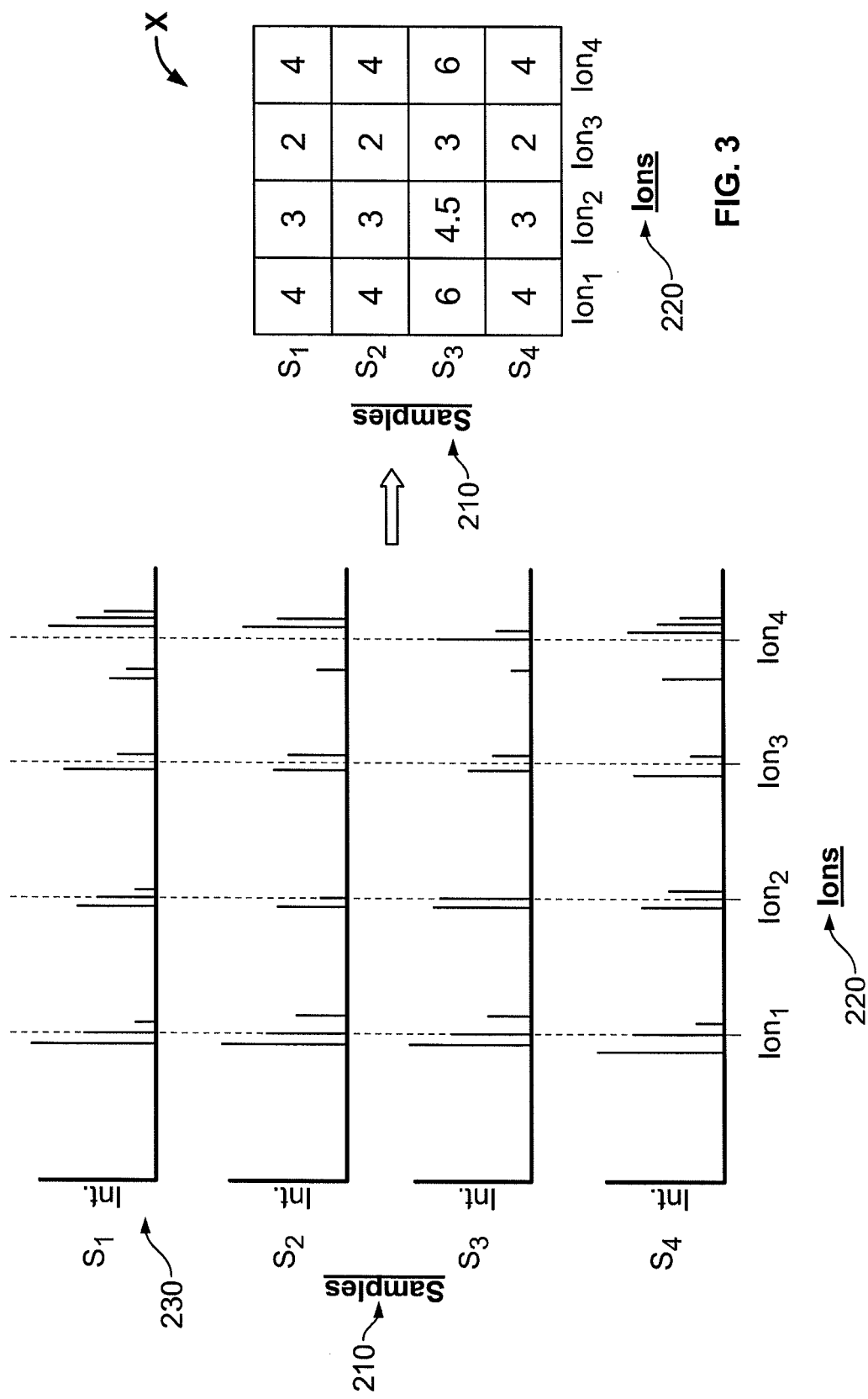

SYSTEM, METHOD, AND COMPUTER PROGRAM PRODUCT FOR ANALYZING SPECTROMETRY DATA TO IDENTIFY AND QUANTIFY INDIVIDUAL COMPONENTS IN A SAMPLE

CROSS-REFERENCE TO RELATED APPLICATIONS

This application claims priority from U.S. Provisional Application No. 60/784,296, filed on Mar. 21, 2006, which is hereby incorporated by reference herein in its entirety.

BACKGROUND OF THE INVENTION

1. Field of the Invention

The present invention relates to the use of non-negative factorization functions and/or correlation functions to determine a characteristic value corresponding to one or more components (such as, for example, metabolites) or other compounds present in a plurality of samples and to use the characteristic value to identify and/or quantify individual components or other components that may be present in the samples.

2. Description of Related Art

The detection of subtle chemical cues in a sample to reveal the presence and corresponding relative quantity of selected components (such as certain small molecules, therapeutic agents, xenobiotics, metabolites, and other substances) has long been a goal of researchers and clinicians. For example, in the field of metabolomics, the small molecules, or metabolites, contained in a human cell, tissue or organ (including fluids) and involved in primary and intermediary metabolism are scrutinized in an attempt to determine the presence and/or identity of such small molecules. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds.

Molecular biology techniques for uncovering the biochemical processes underlying disease in humans have been centered on the human genome, which consists of the genes that make up human DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites, and their role in the human metabolism may be readily identified. In this context, the identification of disease targets may be expedited with greater accuracy than with any other known methods. The collection of metabolomic data for use in identifying disease pathways is generally known in the art, as described generally in U.S. Pat. No. 7,005,255, entitled Methods for Drug Discovery, Disease Treatment, and Diagnosis Using Metabolomics. However, the collection and sorting of metabolomic data taken from a variety of biological samples (i.e., from a patient population) consumes large amounts of time and computational power. For example, according to some metabolomic techniques, spectrometry data for biological samples is collected and plotted in three dimensions and stored in an individual file corresponding to each biological sample. Such spectrometry data consists of known spectra corresponding to the detection of certain ions that may be present in a given sample. While individual ions may be detectable in such spectra, the combinations and interplay of such ions to indicate specific individual metabolite compounds may not be immediately discernable, especially in only a single biological sample.

If the sample subjected to spectrometry contains substantially pure components (such small molecule metabolites, for example), the spectrum of the component can be easily matched with the spectra of known components in order to identify the component. Furthermore, if there is an ion unique to a specific component, then the intensity (as discernible in the spectral plot) of the ion can be used for the relative quantification of the component in the sample. However, in many cases, the fractionation of a particular biological sample (in a liquid or gas chromatograph, for example) is incomplete. For example, two or more component compounds or small molecule components may "co-elute" from the physical separation process giving rise to an impure mixture of components going into the spectrometer. Thus, subtle spectral trends viewed over many individual biological samples of the same type may be indicative of the presence of one or more otherwise-obscured components.

The assignee of the present application, Metabolon, Inc., has developed a system and method for manipulating three-dimensional spectrometry data sets to produce plots that are more directly comparable to a plurality of characteristic plots corresponding to a plurality of selected metabolites, as disclosed in U.S. patent application Ser. No. 11/462,838 entitled A System, Method, and Computer Program Product Using an Automated Relational Database in a Computing System to Compile and Compare Metabolomic Data Obtained from a Plurality of Samples, which is incorporated herein by reference in its entirety. Such characteristic plots may enable a user to subjectively analyze a series of complex data sets in a visual display that may indicate the presence of selected sample components across the group of samples even in cases where the selected components have co-eluted from the physical separation processes prior to spectral analysis. While subjectively comparing deconstructed spectral plots to spectral characteristic plots may be useful for identifying the potential presence of more complex mixtures of components in a given type of biological sample, such subjective comparisons still do not provide quantitative information related to the relative amounts of particular components (such as metabolites, small molecule therapeutic agents, metabolized drugs, and xenobiotics, for example) that may be present in a particular sample.

Furthermore, some analytical methods have been proposed for quantitatively analyzing spectrometry data sets across a group of samples. For example, factor analysis (FA), principal component analyses (PCA), and singular value decomposition (SVD) have been applied to a matrix of spectrometry data from a group of biological samples to generate a small number of basic spectral profiles (corresponding to individual component compounds in the samples), and to calculate the weights with which each of these basic components is present in each individual sample. However, FA, PCA, and SVD analytic methods provide results that are often ambiguous and/or difficult to interpret because the basic spectral profiles may include a number of negative values (having no meaningful analytical value). Thus, post-analysis transformations, requiring additional computing power, time, and skill, are required to glean physically meaningful analytical results from the process. In addition, FA, PCA, and SVD analytical methods do not necessarily yield results that point to independent groups of ions indicative of particular metabolite compounds or other components present in the samples, as described for example by Juvela et al. See Juvela, M., Lehtinen, K. and Paatero, P., "The Use of Positive Matrix Factorization in the Analysis of Molecular Line Spectra from the Thumbprint Nebula (1994)," *Clouds Cores and Low Mass Starts ASP Conference Series*, Vol. 65, pp. 176-180; D. P. Clemens and R. Barvainis, eds.

Therefore, there exists a need for an improved system to solve the technical problems outlined above that are associated with existing metabolomic data analysis systems. More particularly, there exists a need for a system and method capable of analyzing spectrometry data across a group of biological samples to easily and accurately determine: physically-relevant non-negative amounts of each metabolite compound present in the samples, regardless of the co-elution of some metabolite compounds in a particular sample; spectra of the metabolite compounds present in the samples; and a number of metabolite compounds that may be present in the samples. There is also a need for a system and method for de-convoluting mass spectrometry data from a plurality of samples, and/or parent compounds included therein, into the spectra of the pure metabolite compounds present in the samples and determining the relative concentration of the metabolite compounds in the samples.

BRIEF SUMMARY OF THE INVENTION

The needs outlined above are met by the present invention which, in various embodiments, provides a system that overcomes many of the technical problems discussed above, as well other technical problems, with regard to identification and quantification of components (such as metabolites, for example) using spectrometry data from a plurality of biological samples. Specifically, in one embodiment, a system is provided for analyzing spectral data received from an analytical device across a plurality of samples. The analytical device may further include any device that produces data that may be formatted into a 2-way table of samples for rows and measurements for columns. For example, the analytical device may include, but is not limited to: a nuclear magnetic resonance imaging device; a spectrometry device (including for example, gas chromatography mass spectrometers (GC-MS) and liquid chromatography mass spectrometers (LC-MS)); and electrochemical array devices. The system comprises a database in communication with the analytical device for automatically receiving a data matrix corresponding to each of the plurality of samples. The data matrix includes a plurality of rows corresponding to each of the plurality of samples and a plurality of columns corresponding to a plurality of ions present in the samples. The columns also correspond to the plurality of ions that have eluted from each sample at a given point in time in the analytical device. The system also comprises a processor device in communication with the database for determining a characteristic value corresponding to at least one of a plurality of components present in the plurality of samples. The components comprise at least a portion of the plurality of ions present in the samples. In addition, the system also comprises a user interface in communication with the database and the processor device for displaying a visual indication of the characteristic value corresponding to at least one of a plurality of components across the plurality of samples.

According to some system embodiments of the present invention, the processor device may be configured to be capable of performing a non-negative matrix factorization function and/or independent component analysis for determining the characteristic value. For example, the processor device may perform a non-negative matrix factorization function and/or an independent component analysis to determine a characteristic value that may include, but is not limited to: a number of the plurality of components present in the plurality of samples; a relative concentration of at least one of the plurality of components present in each of the plurality of samples; and a spectra of at least one of the plurality of components, the spectra including an indication of at least a portion of the plurality of ions present in the at least one of the plurality of components. In other embodiments, the processor device may also be configured to be capable of performing a correlation function for determining the characteristic value comprising a common spectrum of a particular component across the plurality of samples. The common spectrum includes a combination of at least a portion of the plurality of ions and may correspond to a substantially pure component (such as a particular metabolite of interest) present in the plurality of samples.

Furthermore, in some embodiments the processor device may be further configured to be capable of comparing the spectrum of at least one of the plurality of components to a plurality of known spectra corresponding to a plurality of known components so as to screen the plurality of samples for a presence of the plurality of known components in the plurality of samples. In embodiments wherein the processor device is configured to be capable of performing a correlation function, the processor device may also be further configured to be capable of comparing the common spectrum corresponding to a substantially pure component to a plurality of known spectra corresponding to a plurality of known components so as to screen the plurality of samples for a presence of the plurality of known components in the plurality of samples. According to some such embodiments, the system may also comprise a memory device in communication with the database for storing the plurality of known spectra.

Some embodiments of the present invention also provide a method and/or computer program product for analyzing metabolomics data received from an analytical device across a plurality of samples. Such a method comprises automatically receiving a data matrix corresponding to each of the plurality of samples, wherein the data matrix includes a plurality of rows corresponding to each of the plurality of samples and a plurality of columns corresponding to a plurality of ions present in the samples. The method further comprises determining a characteristic value corresponding to at least one of a plurality of components present in the plurality of samples (wherein the components comprise at least a portion of the plurality of ions). In addition, the method further comprises a step for displaying a visual indication of the characteristic value corresponding to at least one of a plurality of components across the plurality of samples.

According to some method embodiments, the determining step comprises performing a non-negative matrix factorization (NNMF) function for determining the characteristic value. In other embodiments, the determining step comprises performing an independent component analysis (ICA) for determining the characteristic value. According to some such embodiments, the characteristic value determined via the determining step (via NNMF and/or ICA, for example) may include, but is not limited to: a number of the plurality of components present in the plurality of samples; a relative concentration of at least one of the plurality of components present in each of the plurality of samples; and a spectra of at least one of the plurality of components, wherein the spectra includes an indication of at least a portion of the plurality of ions present in the at least one of the plurality of components. Furthermore, in some additional embodiments, the determining step may further comprise performing a correlation function for determining the characteristic value. In such correlation function steps, the characteristic value may comprise a common spectra across the plurality of samples, wherein the common spectra includes a combination of at least a portion of the plurality of ions and wherein the common spectra corresponds to at least one of a substantially pure component present in the plurality of samples and imputed spectra of one or more pure components present in the plurality of samples.

Various embodiments of the present invention may further comprise comparing the characteristic value (generated by the determining step) to a plurality of known spectra corresponding to a plurality of known components so as to screen the plurality of samples for a presence of the plurality of known components therein. For example, in embodiments where the determining step comprises performing a non-negative matrix factorization function, the method may further comprise comparing the spectra of at least one of the plurality of components to a plurality of known spectra corresponding to a plurality of known components so as to screen the plurality of samples for a presence of the plurality of known components therein. Likewise, in embodiments wherein the determining step comprises performing a correlation function to determine a common spectra across the plurality of samples, the method may also further comprise comparing the common spectra corresponding to a substantially pure component to a plurality of known spectra corresponding to a plurality of known components so as to screen the plurality of samples for a presence of the plurality of known components therein.

Thus the systems, methods, and computer program products for compiling and comparing metabolomics data across a plurality of samples, as described in the embodiments of the present invention, provide many advantages that may include, but are not limited to: providing a listing of substantially pure components and their spectra using spectrometry data from a plurality of samples, identifying target elution times or elution time intervals that may be used to partition a data matrix (defined by, for example, rows of samples and columns of ions) into submatrices wherein non-negative matrix factorization functions or independent component analysis factorization functions and/or correlation functions might be performed to determine one or more characteristic values corresponding to potentially masked and/or co-eluted components comprising one or more of the ions, and building a library of known spectra corresponding to various components that may be present in a variety of samples that may be compared to known spectra to identify the component (such as a specific metabolite).

These advantages and others that will be evident to those skilled in the art are provided in the system, method, and computer program product of the present invention.

BRIEF DESCRIPTION OF THE SEVERAL VIEWS OF THE DRAWINGS

Figure 1:
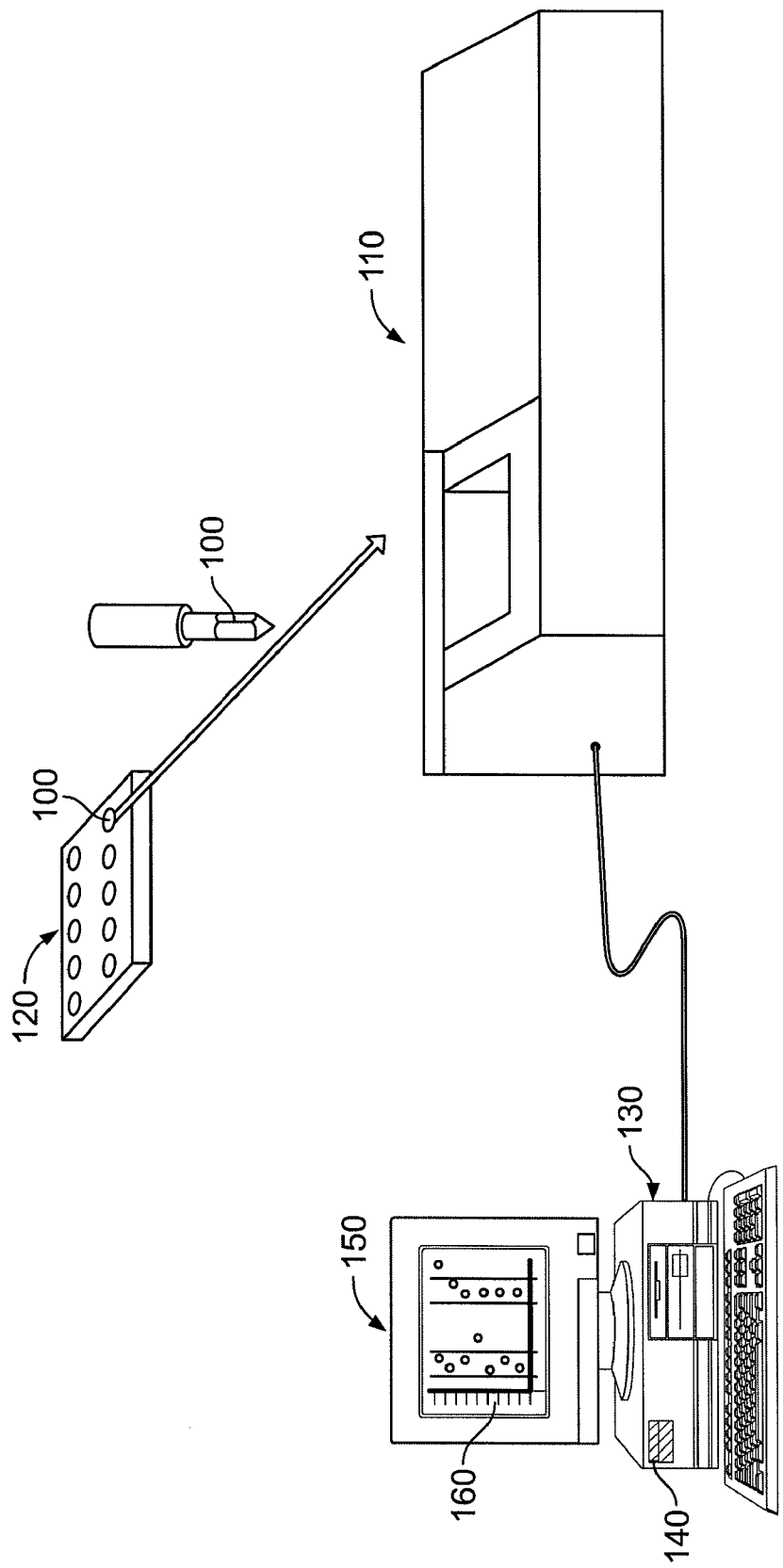

Having thus described the invention in general terms, reference will now be made to the accompanying drawings, which are not necessarily drawn to scale, and wherein:

FIG. 1 illustrates a system according to one embodiment of the present invention having a database, including a memory device and user interface, in communication with a spectrometry device.

FIG. 2 is an illustration of a series of spectra that may be generally indicative of the ions present in a particular series of biological samples.

FIG. 3 is an illustration of a two-dimensional data matrix that may be utilized by the processor device of the present invention for determining a characteristic value corresponding to a component present in a particular series of biological samples.

Figure 4:
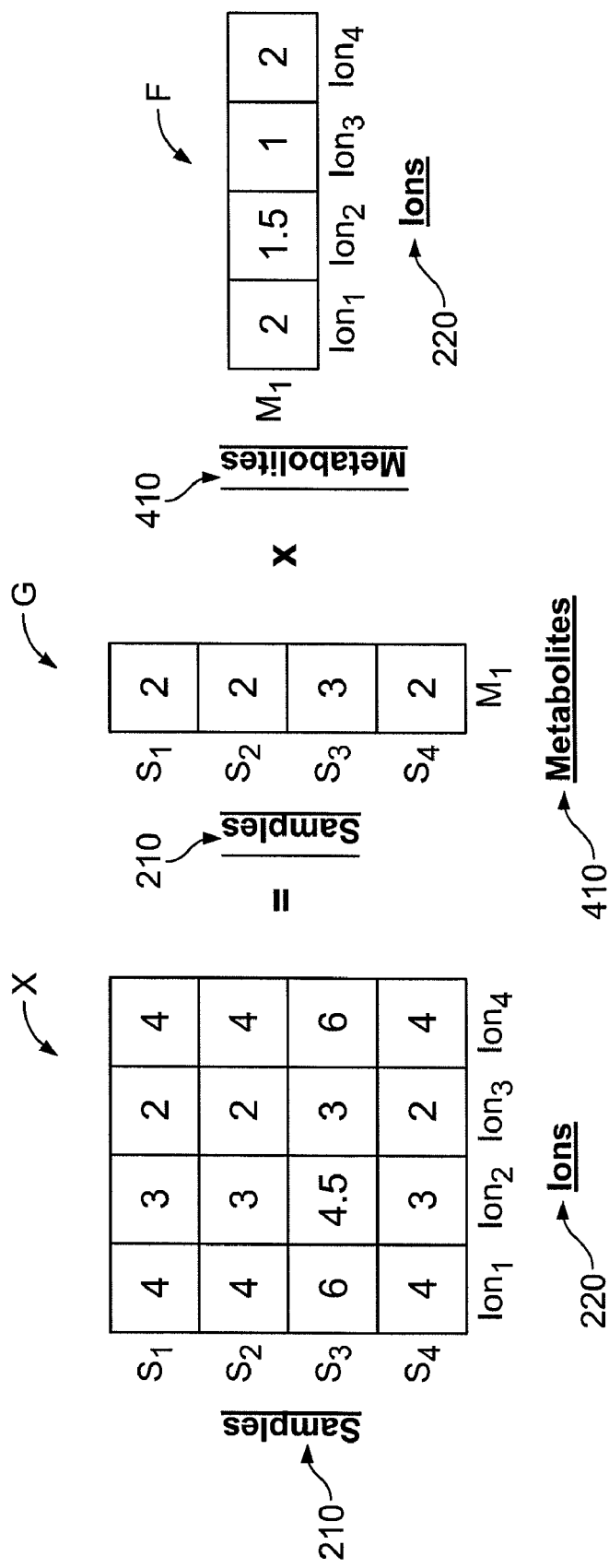

FIG. 4 is an illustration of a factorization function that may be performed by a processor device according to some embodiments of the present invention for determining a characteristic value corresponding to a component present in a particular series of biological samples.

Figure 5:
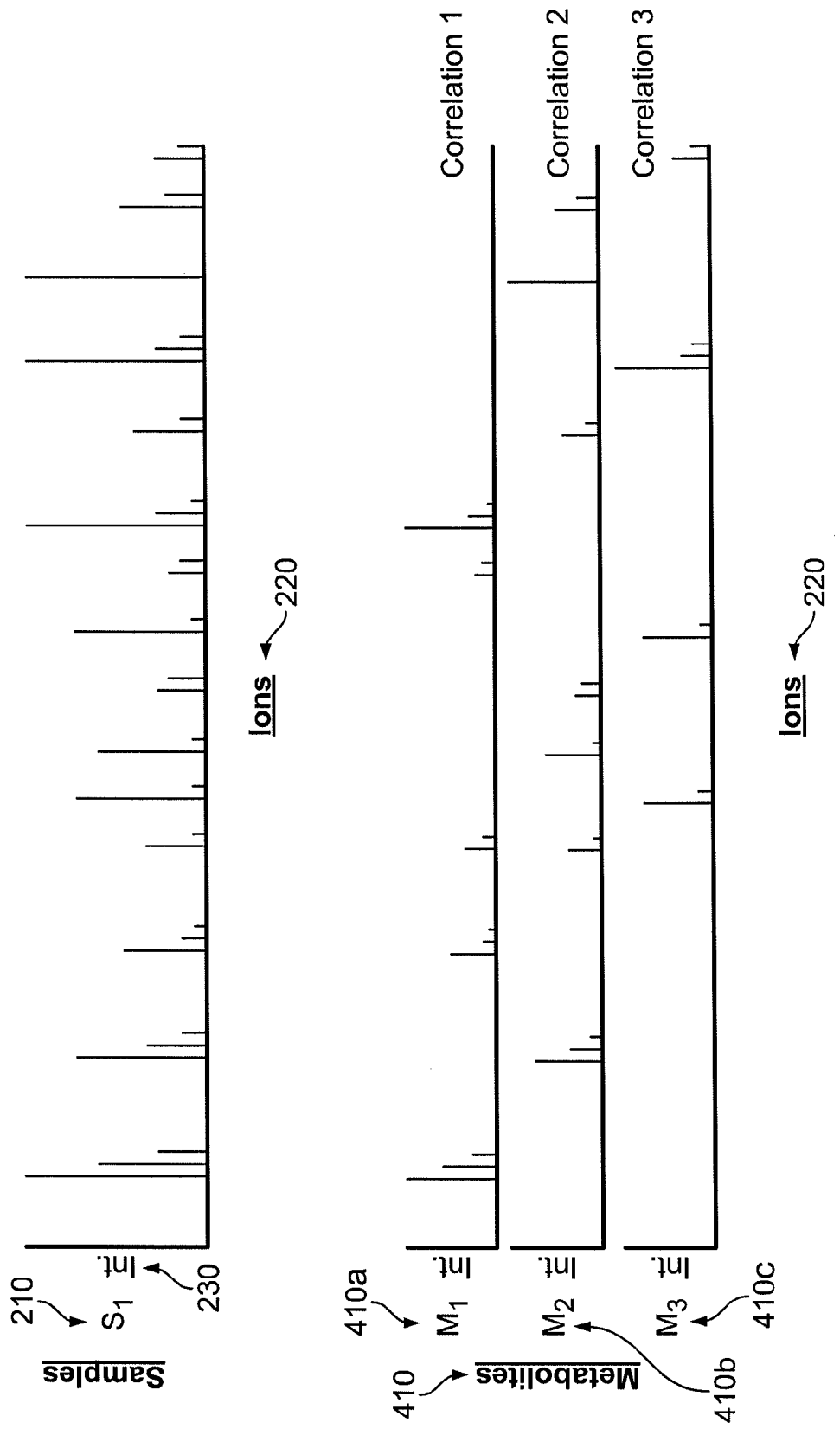

FIG. 5 is an illustration of a correlation function that may be performed by a processor device according to some embodiments of the present invention for determining a characteristic value corresponding to a component present in a particular series of biological samples.

Figure 6:
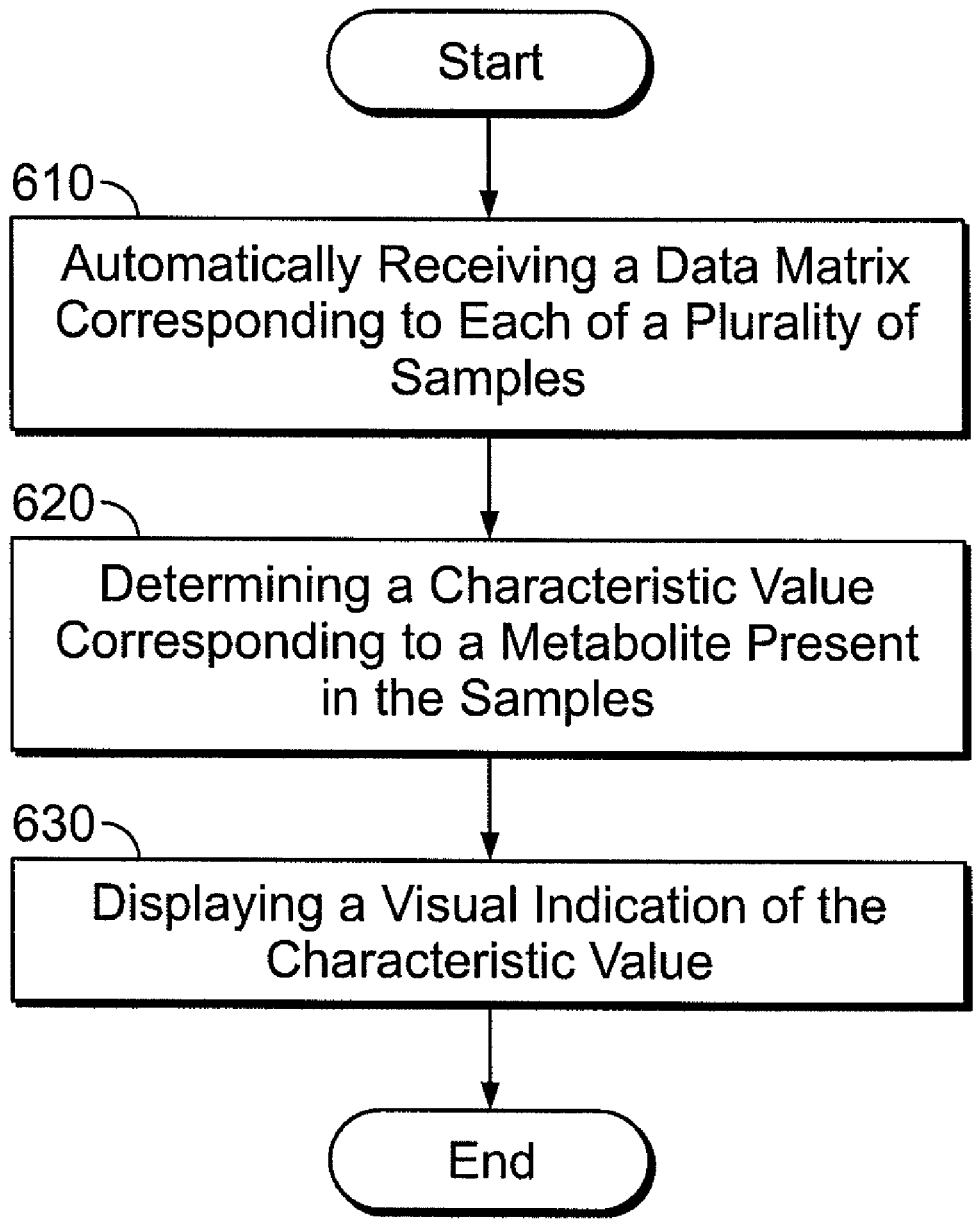

FIG. 6 is a flow-chart illustration of a method according to one embodiment of the present invention including receiving, characteristic value determining, and displaying steps.

Figure 7:
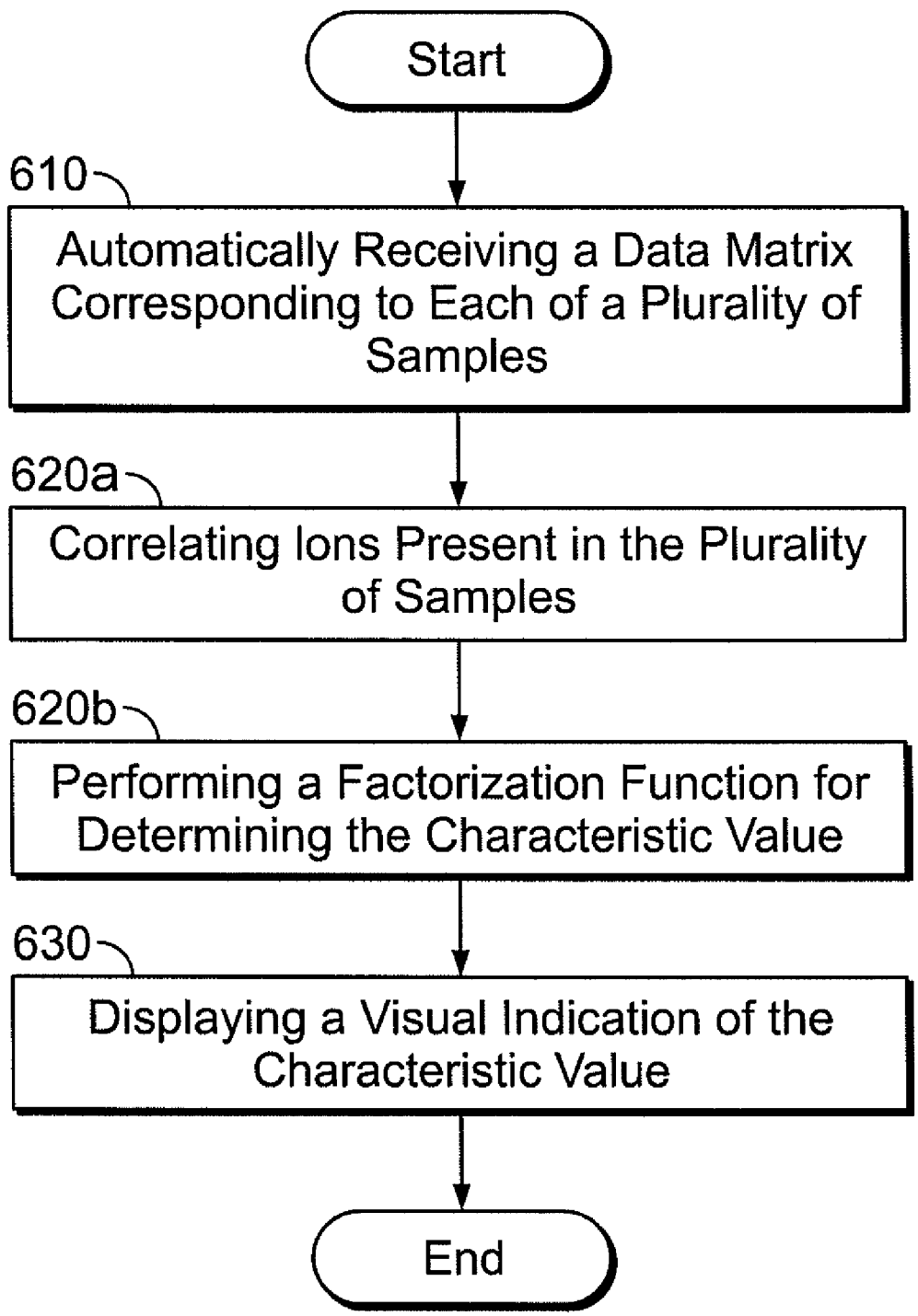

FIG. 7 is a flow-chart illustration of a method according to one embodiment of the present invention including correlation and subsequent factorization steps.

Figure 8:
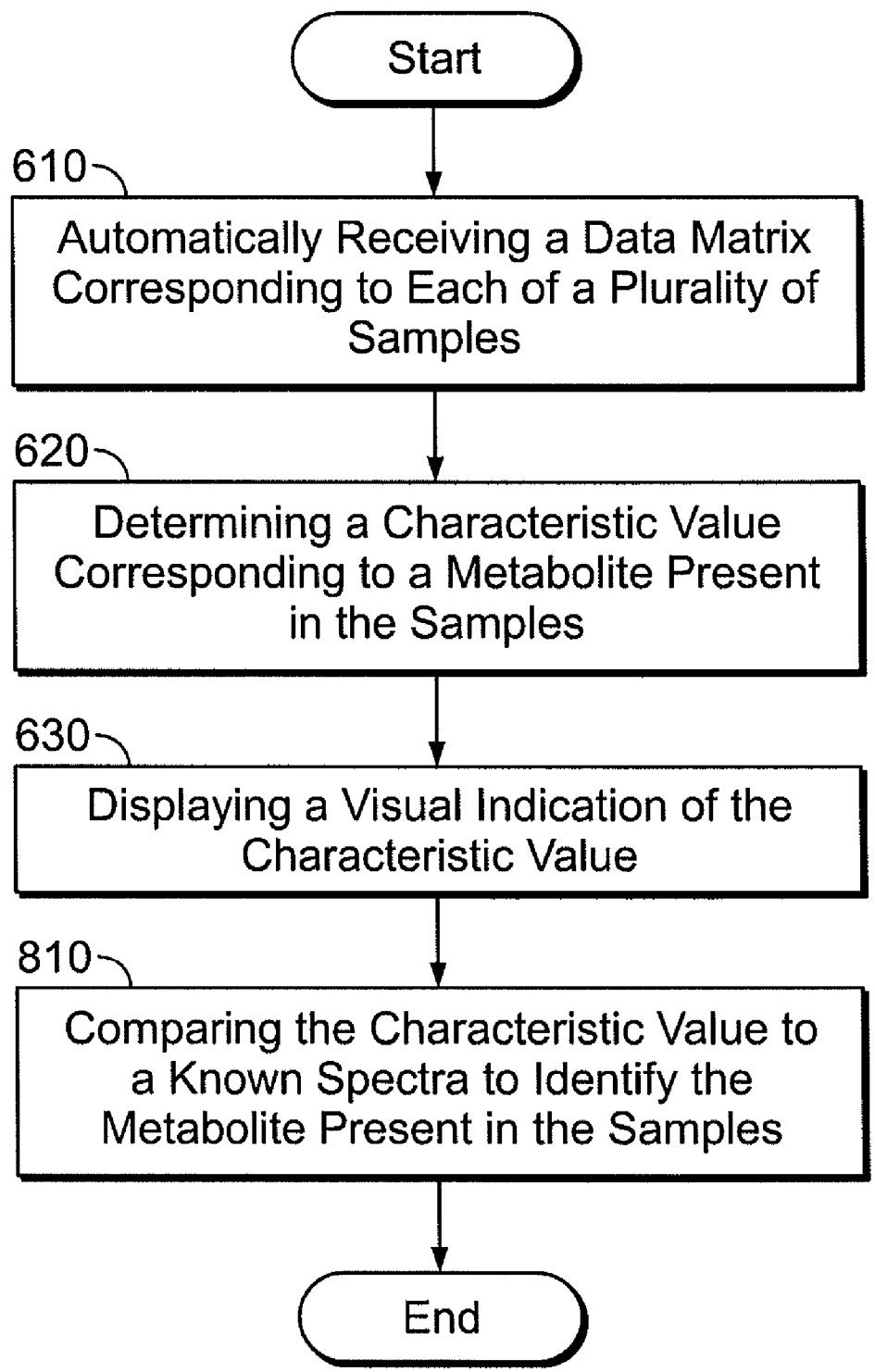

FIG. 8 is a flow-chart illustration of a method according to one embodiment of the present invention including a step for comparing the characteristic value to a known spectra to identify a detected component.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Though the systems, methods, and computer program products of the present invention are described in conjunction with a mass spectrometer used to analyze metabolomic data, one skilled in the art will appreciate that such description is for exemplary purposes only. More particularly, the systems, methods, and computer program products of the present invention can be adapted to any number of processes that are used to generate complex sets of spectral data across a plurality of biological samples. For example, embodiments of the present invention may be used with a variety of analytic devices and processes including, but not limited to: nuclear magnetic resonance imaging (NMR); gas chromatography-mass spectrometry (GC-MS); liquid chromatography-mass spectrometry (LC-MS); and electrochemical arrays (EC).

FIG. 1 illustrates an example of a system according to one embodiment of the present invention wherein the system is in communication with an analytical device such as a mass spectrometer 110. As shown, a biological sample 100 may be introduced at the top of a column of media within the spectrometer 110 and analyzed using mass spectrometric techniques that will be appreciated by those skilled in the art. For example, the components of a particular biological sample 100 may pass through the column of the spectrometer at different elution rates and exhibit different spectral responses based upon their specific characteristics. As will be appreciated by one skilled in the art, the spectrometer 110 may generate a series of spectra corresponding to the ions eluted from each sample at a specific time during the separation process (such as liquid or gas chromatography). An example of such a series of spectra is shown generally in FIG. 2, and plotted as an intensity 230 vs. ion 220 spectra for each sample 210 for each point in time during the separation process. Thus, for a particular elution time range, the spectrometer 110 may also generate a corresponding data matrix X (see FIG. 3, for example) wherein the rows of the matrix X correspond to each particular sample 210 and wherein the columns of the matrix X correspond to each particular ion 220 present in each sample 210. Furthermore, the values populating the matrix X comprise intensity values for each ion 220 present in each sample 210.

According to other embodiments of the present invention, alternate types of analytical devices may be used to generate spectra and the corresponding data matrix X based on an analysis of the series of biological samples 100. For example, the analytical device may include, but is not limited to: nuclear magnetic resonance (NMR) imaging devices, liquid and/or gas chromatography-mass spectrometry devices (LG-MS and/or CG-MS), electrochemical array (EC) devices, and/or combinations of these devices. One skilled in the art will appreciate that such spectra and corresponding data matrix X may be generated by other appropriate analytical devices that may be in communication with components of the system of the present invention as described in further detail below.

A plurality of biological samples 100 may be taken individually from a well plate 120 and/or from other types of sample containers and introduced individually into the analytical device 110 for analysis and generation of the three-dimensional data set (see FIG. 2a). For example, individual biological samples 100 may be transferred from a well plate 120 to the analytical device 110 via pipette, syringe, microfluidic passageways defined in a test array, and/or other systems for transferring biological samples in a laboratory environment. The biological samples may include, but are not limited to: blood samples, urine samples, cell cultures, saliva samples, and/or other types of biological samples in which the components (such as metabolites, for example) and/or chemical components of interest may be present.

As shown in FIG. 1, embodiments of the present invention may comprise a database (housed, for example in a memory device 140) in communication with a processor device 130 (such as a computer device, for example), which is further configured to be in communication with the analytical device 110 for automatically receiving a data matrix X (see FIGS. 3 and 4) corresponding to each of the plurality of samples 210. As described above, and as shown in FIG. 3, the data matrix X may include a plurality of rows corresponding to each of the plurality of samples 210 and a plurality of columns corresponding to a plurality of ions 220 present in the samples 210. The processor device 130 may be in communication with the analytical device 110 via wire (RS-232, and/or other types of wire connection) and/or wireless (such as, for example, RF, IR, or other wireless communication) techniques such that the database housed therein (and/or in communication therewith) may receive the data matrix X from the analytical device 110. Furthermore, the analytical device 110 may be in communication with one or more processor devices 130 (and associated user interfaces 150) via a wired and/or wireless computer network including, but not limited to: the internet, local area networks (LAN), wide area networks (WAN), or other networking types and/or techniques that will be appreciated by one skilled in the art. The database may be structured using commercially-available software, such as, for example, Oracle, Sybase, DB2, or other database software. As shown in FIG. 1, the database (and/or processor device 130 housing said database) may be in further communication with a memory device 140 (such as a hard drive, memory chip, flash memory, RAM module, ROM module, and/or other memory device 140) for storing known spectra (for use in the comparing step 810, shown for example, in the flow chart of FIG. 8) and data matrices (such as, for example, matrix X automatically received from the analytical device 110). In addition, the memory device 140 may also be used to house other data received by the database and/or manipulated by the processor device 130. Furthermore, and as described in further detail below, the memory device 140 may also be configured to store characteristic values determined by the processor device 130 of the present invention, such as, for example, the contents and structure of result matrices G and F (as shown in FIG. 4), and the common spectra generated by the processor device when performing a correlation function across the plurality of samples 210 (see elements 410a, 410b, and 410c of FIG. 5).

The processor device 130 is capable of utilizing the data matrix X (see FIG. 3) received by the database 130 to determine a characteristic value corresponding to at least one of a plurality of components present in the plurality of samples 210 wherein the components include some combination of at least a portion of the plurality of ions 220. Furthermore, as shown in FIG. 1, embodiments of the present invention may also comprise a user interface 150 in communication with the database (and/or memory device 140 and the processor device 130 for displaying a visual indication (see, for example, the first and second result matrices, G and F, respectively, of FIG. 4) of the characteristic value corresponding to at least one of a plurality of components across the plurality of samples 210.

In some system embodiments of the present invention, the processor device 130 may be configured to be capable of performing a factorization function (see generally, FIG. 4) for determining the characteristic value. According to various embodiments, the factorization function performed by the processor device 130 may include, but is not limited to: non-negative matrix factorization (NNMF) (also called "positive matrix factorization" (PMF)); and/or independent component analysis (ICA) factorization. Some examples of NNMF functions that may be performed by the processor device 130 according to various embodiments of the present invention include those functions described generally in the article entitled "Learning the Parts of Objects by Non-Negative Matrix Factorization" by Lee and Seung (See Lee, Daniel D. and Seung, H. Sebastian, "Learning the Parts of Objects by Non-Negative Matrix Factorization," *Nature*, Vol. 401, pp. 788-791 (Oct. 21, 1999).), the contents of which are incorporated by reference herein in their entirety. Additional NNMF functions that may be utilized by the processor device 130, according to other embodiments of the present invention, are described by Lee and Seung in an additional reference (see Lee, Daniel D. and Seung, H. Sebastian, "Algorithms for Non-Negative Matrix Factorization," *Advances in Neural Information Processing Systems* 13, pp. 556-562 (2001).), the contents of which are also incorporated by reference herein in their entirety. Furthermore, a survey of additional NNMF functions that may alternatively be performed by the processor device 130, according to other embodiments of the present invention, is provided by Tropp (see Tropp; Joel A., "Literature Survey: Non-negative matrix factorization," (EE381K-14 Multidimensional Digital Signal Processing— Spring 2003 Projects), The University of Texas at Austin, (2003).), the contents of which are also incorporated herein by reference in their entirety.

In other embodiments, ICA functions may be used by the processor device 130 for performing the factorization. Exemplary ICA functions are described, for example, by Hyvärinen et al (see Hyvärinen, A., Karhunen, J., and Oja, E., *Independent Component Analysis*, John Wiley & Sons (2001).), the contents of which are also incorporated herein by reference in their entirety.

In such embodiments, the characteristic value determined by the factorization function may include, but is not limited to: a number of the plurality of components (such as, for example, metabolite compounds) present in the plurality of samples (as indicated by the number of columns 410 in the first result matrix G); a relative concentration of at least one of the plurality of components present in each of the plurality of samples (for example, each column 410 of the first result matrix G generally indicates the relative concentration of each component 410 component in the samples 210); and a spectra (by individual ion 220) of at least one of the plurality of components 410, the spectra including an indication of at least a portion of the plurality of ions 220 present in the at least one of the plurality of components 410 (as shown in the second result matrix F).

The processor device 130 may perform the factorization function using a data matrix X as an input (see FIG. 3) wherein the columns of the matrix X correspond to different ions 220 (further corresponding to different channels of a spectrometer or other analytical device 110). As discussed above, the rows of matrix X correspond to the various samples 210 from which the matrix X data is taken. Specifically, the processor device 130 may, in some embodiments, solve a bilinear factorization problem as expressed in the following equation:

$$X=GF; \quad (1)$$

wherein X is the input matrix X (where X consists of, for example, n rows and p columns). Furthermore, G and F represent the first and second result matrices (where G consists of n rows and k columns and where F consists of k rows and p columns). One skilled in the art will appreciate that k is typically less than p and that k may be determined, for example, from a Scree plot from a SVD of the input matrix X. An exemplary set of result matrices G, F (resulting from an exemplary data matrix X) is shown, for example in FIG. 4.

Furthermore, in some embodiments, the processor device 130 may also generate an estimate of error E (wherein E may be expressed as E=X−FG) in the individual ion 220 amounts using the factorization function. The resulting error estimates for each ion 220 may also be entered into an error matrix S. Using the resulting data and error matrices X and S, respectively, the processor device 130 may be configured to be capable of calculating first and second result matrices G, F as a least squares solution which minimizes the error expressed as:

$$\Sigma_{i,j}(((X-GF)_{i,j})/S_{i,j})^2; \quad (2)$$

wherein the solution is further restricted in that every element of the result matrices G and F is required to be non-negative. There are various other criteria that may also be optimized to determine G and F, as outlined, for example, by Lee and Seung. These constraints ensure that the processor device 130 generates characteristic values having positive basic components such that the spectra of components 410 within the samples may be reconstructed by the matrix multiplication of G and F. G may be used to estimate the relative concentrations of the substantially pure components with the samples and F reveals the ion sets and the relative intensities of the spectra of the substantially pure components, as described further herein.

One skilled in the art will appreciate that the result matrices G and F are not unique and may be modified and still reproduce X. For example, in some alternative embodiments, the processor device 130 may reproduce X according to the relationship expressed as:

$$X=GS^{-1}SF; \quad (3)$$

wherein S is a k×k matrix and $S^{-1}$ is its inverse. S may be selected to enhance the interpretability of the result matrices G and F. According to other embodiments, the factorization function may be alternatively expressed as:

$$X=GDF; \quad (4)$$

Wherein D is a k×k matrix (which may also be selected to enhance the interpretability of the result matrices G and F).

FIG. 4 shows a simplified set of result matrices G, F produced by the processor device 130 according to one example of a factorization function (specifically, NNMF and/or ICA). In FIG. 4, the sample set 210 contains only a single component 410 (indicated by the single column of result matrix G. In the example shown, result matrix G comprises a column vector with four rows corresponding to the four concentrations, one in each of the four samples 210, (see FIG. 3, for example) generated by the analytical device 110 for four samples 210. Furthermore, result matrix F is a row vector with four columns corresponding to the ion intensities detected by the analytical device 110 for each of the four ions 220. The processor device 130 seeks to populate the result matrices G, F in order to approximate the data matrix X such that each row of X (corresponding to the various samples 210 in the analysis) should be approximately equal to F (which provides the intensities ("heights," for example) of the various ions 220 in the single component 410 present in the samples) multiplied by result matrix G (which provides an indication of a relative concentration of at least one of the plurality of components 410 present in each of the plurality of samples 210). In the simplified case of FIG. 4, the resulting "valley" shape in result matrix F is the weighted average of all ion spectra 220 in the single component 410 present. It should be understood, however, that the processor device 130 may also be capable of performing an NNMF process with more complicated sets of samples such that the result matrix F is indicative of a larger number of components 410. For example, every NNMF process performed by the processor device 130 may be considered as a sum of NNMF processes of rank one (i.e. the result matrix F includes additional rows indicating the presence of additional components 410). Furthermore, result matrix G may include additional columns to indicate characteristic values comprising the corresponding concentrations of each component in each of the plurality of samples 210.

As one skilled in the art will appreciate, the factorization function, defined in one embodiment by Equation (1), is performed using ion spectra 220 across the plurality of samples 210 (as defined by matrix X) at a particular elution time (where "elution time" refers to the time at which the particular ion spectra 220 are observed using the analytical device 110). The processor device 130 may further be configured to repeat the performance of the factorization function described above for a number of elution times until the error function (see Equation (2), for example) is minimized for a particular combination of elution time, data matrix X (which will vary based on the elution time), and result matrices G, F. While such a process will eventually yield the characteristic value corresponding to most (if not all) of the components 410 present in the plurality of samples 210, the repetition of the factorization function (as shown in FIG. 4) across a broad range of elution times and for a large number of samples 210 may be expedited in some embodiments by selecting a specific elution time and/or a relatively narrow range of elution times over which the factorization function may be performed to determine the characteristic value or values.

For example, in some embodiments of the present invention, the processor device 130 may be configured to be capable of correlating the plurality of ions 210 by the corresponding elution time to generate a data matrix (see data matrix X, for example) corresponding to each of the plurality of samples 210 at the particular elution time. As described herein, the data matrix X may include a plurality of rows corresponding to each of the plurality of samples 210 and a plurality of columns corresponding to the plurality of ions 220 present in the respective samples 210. In such embodiments, the ions 220 may be first grouped by elution time to identify a starting point for the subsequent performance of a factorization function (see Equations (1) and (2), for example) by the processor device 130. Correlating the ions 210 by elution time may thus provide an initial estimation as to which ions 210 may be associated with one another as components of a component 410 of interest. This initial estimate may be used on its own or as an initial estimate for the result matrix G in the factorization function. According to some embodiments, a plurality of parallel processor devices 130 may be utilized to analyze the various matrices X that may correspond to a plurality of elution times and/or elution time ranges such that computation of the result matrices G and F may be expedited.

Once a particular elution time and/or range of elution times is chosen, the matrix X of ion spectra 220 versus sample 210 may be constructed and analyzed by the processor device 130 using a factorization function as described above, in order to determine a characteristic value based at least in part on the intensity of the portion of the plurality of ions 220. As described above, the characteristic value may correspond to at least one of a plurality of components 410 present in the plurality of samples 210, wherein the components 410 comprise at least two of the portion of the plurality of ions 220.

According to other embodiments of the present invention, the processor device 130 may also be configured to be capable of correlating ion spectra 210 (see FIG. 2, for example) at a specific elution time across a plurality of samples 220. In such embodiments, the processor device 130 may correlate the relative rise and fall of ion spectra across samples at a specific elution time. For example, and as shown in the spectral plots of FIG. 5, the processor device 130 may be configured to be capable of performing a correlation function for determining the characteristic value, wherein the characteristic value comprises a common spectra 410a, 410b, 410c across the plurality of samples 210. The common spectra 410a, 410b, 410c may include a combination of at least a portion of the plurality of ions 220 and corresponding to a component 410 present in the plurality of samples 210.

For example, as shown in FIG. 5, the processor device may correlate the rise and fall of the intensity 230 of certain ions 220 across multiple samples 210. The processor device 130 may be configured to be capable of detecting common spectra (see element 410a, for example) that may be evident across a number of samples and presenting such a common spectrum 410a, as one of several characteristic values that may correspond to selected components 410 that may be present in the plurality of samples 210. In some embodiments, as shown in FIG. 5, the processor device may perform a correlation function across a plurality of samples that results in the identification of three separate common spectra 410a, 410b, 410c that may correspond, for example, to three distinct components 410 that may be present in the sample group. The common spectra 410a, 410b, 410c characteristic values generated by the processor device as part of the correlation function may be directly comparable to the result matrix F generated by the processor device 130 in embodiments wherein the processor device 130 performs a factorization function (as described generally above with respect to FIG. 4). Thus, in some embodiments, the processor device 130 may be further capable of comparing a characteristic value generated by a correlation function (such as a common spectrum 410a, for example) with a characteristic value generated by a factorization function (such as the result matrix F, as shown in FIG. 4) because each of these characteristic value types is comparable as a spectrum of ions 220 making up a particular component 410 found within the sample 210 set.

In some embodiments, the processor device 130 may further be configured to be capable of comparing the spectra (as defined by, for example, the various rows of the result matrix F) of at least one of the plurality of components 410 to a plurality of known spectra corresponding to a plurality of known components so as to screen the plurality of samples 210 for a presence of the plurality of known components in the plurality of samples 210. In a similar manner, the processor device 130 may be further configured to be capable of comparing the common spectra (see element 410a of FIG. 5, for example) corresponding to a component 410 present in the plurality of samples 210 to a plurality of known spectra corresponding to a plurality of known components so as to screen the plurality of samples 210 for a presence of the plurality of known components in the plurality of samples 210.

For example, in some system embodiments, the processor device 130 may comprise and/or be configured to be in communication with a memory device 140 (such as a hard drive, memory chip, flash memory, RAM module, ROM module, and/or other memory device 140) for storing known spectra (for use in the comparing step 810, shown din the flow chart of FIG. 8) associated with known components. Thus, the processor device 130 may be capable, not only of determining the characteristic value (such as a spectra or result matrix, as described above), but also comparing the characteristic value to a known one of a plurality of known spectra stored in a library of known components in the memory device 140. Thus, embodiments of the present invention may be especially useful in identifying components 410 that may be obscured and/or not readily-detectable in a particular sample or group of samples 210 using subjective non-quantitative methods. For example, some embodiments of the present invention may be used to identify a pattern of ions that are not present in an historical collection or existing library of ion patterns. The identification of such patterns may be suggestive of the presence of a compound that is unknown to the system of the present invention (such as a non-metabolite drug).

Furthermore, the memory device 140 may also be configured to store characteristic values determined by the processor device 130 of the present invention, such as, for example, the contents and structure of result matrices G and F (as shown in FIG. 4), and the common spectra generated by the processor device when performing a correlation function across the plurality of samples 210 (see elements 410*a*, 410*b*, and 410*c* of FIG. 5). Thus, embodiments of the present invention may also be capable of storing characteristic values determined by the processor device 130 when performing, for example, the factorization and/or correlation functions described above in order to build a library of unknown components 410 (containing a plurality of ions 220 as shown in the result matrix F, for example) that may be associated with a particular disease state or other attribute associated with one or more of the plurality of samples 210.

As described with respect to FIG. 1, embodiments of the present invention may comprise a user interface 150 in communication with said processor device 130 for displaying a visual indication of the characteristic value corresponding to at least one of a plurality of components 410 across the plurality of samples 210. For example, as shown in FIG. 4, the user interface 150 may be capable of displaying one or both the result matrices G, F produced by the processor device using a factorization function. In some embodiments, the user interface 150 (in combination with the processor device 130) may be capable of converting the various rows of the result matrix F into a spectrum output of the ions 220 making up the various components 410 present in the plurality of samples 210. Furthermore, as shown in FIG. 5, the user interface 150 may also be capable of displaying one or more of the common spectra (as a chart of intensity 230 versus ion 220, for example) generated by the processor device when performing a correlation function across the plurality of samples 210 (see elements 410*a*, 410*b*, and 410*c* of FIG. 5). According to some embodiments, the user interface 150 may comprise a display device, personal computer, and/or other electronic device having a display for graphical representation of various types of data including, but not limited to, the characteristic values determined by the processor device 130 of the embodiments described herein.

As shown in FIGS. 6-8, embodiments of the present invention also include methods for analyzing metabolomics data received from an analytical device 110 across a plurality of samples 210 (see FIG. 2, for example). According to one embodiment, shown in FIG. 6, the method comprises a step 610 of automatically receiving a data matrix X corresponding to each of the plurality of samples 210. As shown, for example, in FIG. 3, the data matrix X includes a plurality of rows corresponding to each of the plurality of samples 210 and a plurality of columns corresponding to a plurality of ions 220 present in the respective samples 210. The embodiment of FIG. 6 further comprises a step 620 for determining a characteristic value (which may comprise, for example a relative intensity, concentration, and/or identity of a component 410 and/or ion component 220 of such a component 410, as discussed further below) corresponding to at least one of a plurality of components 410 present in the plurality of samples 210, wherein the components comprise at least a portion of the plurality of ions 220. In addition, the embodiment shown in FIG. 6 further comprises a step 630 for displaying a visual indication of the characteristic value corresponding to at least one of a plurality of components 410 across the plurality of samples 210.

As described with respect to the processor device 130 of certain embodiments of the present invention, the step 620 for determining the characteristic value may comprise performing a factorization function (such as, for example, a NNMF function as defined by Equations (1) and (2) and/or an ICA function) for determining the characteristic value. According to various embodiments of the present invention, the factorization function performed in the characteristic value determining step 620 may include, but is not limited to: non-negative matrix factorizations (NNMF), positive matrix factorizations (PMF), independent component analysis (ICA), and/or combinations of such factorization functions.

In some embodiments, the characteristic value generated in the characteristic value determining step 620 may comprise a number of the plurality of components 410 present in the plurality of samples 210. The number of the plurality of components 410 present in the plurality of samples 210 may be displayed in the displaying step 630, for example, as a number of rows in result matrix F (shown in FIG. 4). In addition, the number of the plurality of components 410 present in the plurality of samples 210 is also generated as a product of such a factorization function and is discernible as the number of columns in result matrix G (as shown in FIG. 4, which depicts a relatively simple single-component characteristic value).

In some embodiments, the characteristic value generated in the characteristic value determining step 620 may comprise a relative concentration of at least one of the plurality of components 410 present in each of the plurality of samples (as shown, for example in the result matrix G that may be generated using a factorization function as defined above by Equations (1) and (2)). For example, the result matrix G (as shown, for example in FIG. 4), generated in the characteristic value determining step 620 according to some embodiments of the present invention, comprises a two-dimensional matrix including rows corresponding to the plurality of samples 210 under investigation and columns corresponding to the concentration of each of the plurality of components 410 present in the plurality of samples 210.

In other embodiments, the characteristic value generated in the characteristic value determining step 620 may also comprise a spectra of at least one of the plurality of components 410, the spectra including an indication of at least a portion of the plurality of ions 220 present in the at least one of the plurality of components 410. For example, as shown in FIG. 4, the numerical elements of the result matrix F represent the intensity spectrum of the single component 410 present in the depicted example. The relative numerical elements in matrix F may thus be plotted to generate a spectra of at least one of the plurality of components 410 present in the plurality of samples 210.

As described above with respect to the processor device 130 of embodiments of the present invention, the characteristic value determining step 620 may also comprise performing a correlation function for determining the characteristic value. In such embodiments, (the results of which are shown in FIG. 5), the characteristic value comprises a common spectra (see, for example, elements 410*a*, 410*b*, 410*c* of FIG. 5) across the plurality of samples 210. As discussed above, at least one of the common spectra 410*a*, 410*b*, 410*c* generated by the performance of a correlation function in the characteristic value determining step 620 may correspond to the rows of result matrix F generated by embodiments of the present invention wherein the characteristic value determining step 620 comprises the performance of a factorization function.

Thus, various embodiments of the present invention may be used together in order to cross-check and/or ensure the accuracy of the characteristic value determining step 620. For example, the common spectra 410a, 410b, 410c generated by the performance of a correlation function may be compared directly to the result matrix F generated by the performance of a factorization function to ensure that all of relevant characteristic values corresponding to a plurality of components 410 present in the plurality of samples 210 are revealed and displayed (step 630) to a user of the systems and methods of the present invention.

As described with respect to some embodiments, utilizing a factorization function (as defined by Equations (1) and (2) discussed above, for example) to determine the characteristic value as part of the characteristic value determining step 620 may be further optimized by utilizing a correlation function to select particular elution times and/or elution time intervals during which the factorization function should be applied. For example, as shown in FIG. 7, embodiments of the present invention may comprise a step 610a for automatically receiving a data set. In such an embodiment, the data set may be more complex that the generally two-dimensional data matrix X received in the receiving step 610 (shown in FIG. 6) in that the data set may also include elution time information and intensity information corresponding to at least a portion of the plurality of ions 220 across the plurality of samples 210.

In order to simplify the data set received in the further receiving step 610a, some method embodiments of the present invention may comprise a step 620a for correlating the plurality of ions in the data set by the corresponding elution time to generate a data matrix (see, for example, element X shown in FIG. 3) corresponding to each of the plurality of samples 210 at the elution time. The resulting data matrix X therefore includes a plurality of rows corresponding to each of the plurality of samples 210 and a plurality of columns corresponding to the plurality of ions 220 present in the respective samples 210. Once the data matrix X has been assembled, a step 620b may be performed, comprising performing a factorization function on the data matrix X for determining a characteristic value based at least in part on the intensity of the portion of the plurality of ions 210. As described with respect to embodiments shown, for example, in FIG. 6, the characteristic value may correspond to at least one of a plurality of components 410 present in the plurality of samples 210, wherein the components comprise at least two of the portion of the plurality of ions 220. As also described with respect to FIG. 6, such a method may also further comprise a step 630 for displaying a visual indication of the characteristic value corresponding to at least one of the plurality of components 410 across the plurality of samples 210.

As shown in FIG. 8, embodiments of the present invention may further comprise a step 810 for comparing the spectra of at least one of the plurality of components 410 (as discernible, for example from result matrix F and/or from the common spectra 410a, 410b, 410c generated by a correlation function) to a plurality of known spectra corresponding to a plurality of known components so as to screen the plurality of samples 210 for a presence of the plurality of known components in the plurality of samples 210.

In addition to providing apparatuses and methods discussed herein, embodiments of the present invention also include associated computer program products for performing the operations described herein. The computer program products have a computer readable storage medium with computer readable program code embodied in the medium. With reference to FIGS. 6-8, the computer readable storage medium may be part of the memory device 140, and may implement the computer readable program code to perform the above discussed operations.

In this regard, FIGS. 6-8 are block diagram illustration of certain methods, systems and computer program products according to some embodiments of the present invention. It will be understood that each block or step of the block diagram and combinations of blocks in the block diagram can be implemented by computer program instructions. These computer program instructions may be loaded onto a computer or other programmable apparatus to produce a machine, such that the instructions which execute on the computer or other programmable apparatus implement the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instructions which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations for performing the specified functions, combinations of steps for performing the specified functions, and program instructions for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for analyzing data received from an analytical device across a plurality of samples, the system comprising:
a database in communication with the analytical device for automatically receiving a data matrix corresponding to each of the plurality of samples, the data matrix including a plurality of rows corresponding to each of the plurality of samples and a plurality of columns corresponding to a plurality of ions present in the respective samples;
a processor device in communication with said database for determining a characteristic value corresponding to at least one of a plurality of components present in the plurality of samples, the components comprising at least a portion of the plurality of ions; and a user interface in communication with said database and said processor device for displaying a visual indication of the characteristic value corresponding to at least one of a plurality of components across the plurality of samples.

2. A system according to claim 1, wherein the processor device is configured to be capable of performing a factorization function for determining the characteristic value, and wherein the characteristic value is selected from the group consisting of:

a number of the plurality of components present in the plurality of samples;

a relative concentration of at least one of the plurality of components present in each of the plurality of samples; and a spectra of at least one of the plurality of components, the spectra including an indication of at least a portion of the plurality of ions present in the at least one of the plurality of components.

3. A system according to claim 2, wherein the factorization function comprises a non-negative matrix factorization.

4. A system according to claim 2, wherein the factorization function comprises an independent component analysis factorization.

5. A system according to claim 1, wherein the processor device is configured to be capable of performing a correlation function for determining the characteristic value, and wherein the characteristic value comprises a common spectra across the plurality of samples, the common spectra including a combination of at least a portion of the plurality of ions and corresponding to at least one of the plurality of components present in the plurality of samples.

6. A system according to claim 2, wherein the processor device is further configured to be capable of comparing the spectra of at least one of the plurality of components to a plurality of known spectra corresponding to a plurality of known components so as to screen the plurality of samples for a presence of the plurality of known components in the plurality of samples.

7. A system according to claim 5, wherein the processor device is further configured to be capable of comparing the common spectra corresponding to a substantially pure component to a plurality of known spectra corresponding to a plurality of known components so as to screen the plurality of samples for a presence of the plurality of known components in the plurality of samples.

8. A system according to claim 6, further comprising a memory device in communication with said database for storing the plurality of known spectra.

9. A system according to claim 7, further comprising a memory device in communication with said database for storing the plurality of known spectra.

10. A system according to claim 1, wherein the analytical device is at least one of:

a nuclear magnetic resonance imaging device;

a spectrometry device;

an electrochemical array device; and combinations thereof.

11. A system for analyzing data received from an analytical device across a plurality of samples, the system comprising:

a database in communication with the analytical device for automatically receiving a data set, the data set being indicative of the presence of a plurality of ions in the samples, the data set including an elution time and an intensity corresponding to at least a portion of the plurality of ions across the plurality of samples;

a processor device in communication with said database for manipulating the data set;

wherein said processor device correlates the plurality of ions by the corresponding elution time to generate a data output matrix corresponding to each of the plurality of samples at the elution time, the data matrix including a plurality of rows corresponding to each of the plurality of samples and a plurality of columns corresponding to the plurality of ions present in the respective samples; and wherein said processor device performs a factorization function on the data matrix for determining a characteristic value based at least in part on the intensity of the portion of the plurality of ions, the characteristic value corresponding to at least one of a plurality of components present in the plurality of samples, the components comprising at least two of the portion of the plurality of ions; and a user interface in communication with said database and said processor device for displaying a visual indication of the characteristic value corresponding to at least one of the plurality of components across the plurality of samples.

12. A method for analyzing data received from an analytical device across a plurality of samples, the method comprising:

automatically receiving, by a database, a data matrix corresponding to each of the plurality of samples, the data matrix including a plurality of rows corresponding to each of the plurality of samples and a plurality of columns corresponding to a plurality of ions present in the respective samples;

determining, by a processor device, a characteristic value corresponding to at least one of a plurality of components present in the plurality of samples, the components comprising at least a portion of the plurality of ions; and displaying, by a user interface, a visual indication of the characteristic value corresponding to at least one of a plurality of components across the plurality of samples.

13. A method according to claim 12, wherein the determining step comprises performing a factorization function for determining the characteristic value and wherein the characteristic value is selected from the group consisting of:

a number of the plurality of components present in the plurality of samples;

a relative concentration of at least one of the plurality of components present in each of the plurality of samples; and a spectra of at least one of the plurality of components, the spectra including an indication of at least a portion of the plurality of ions present in the at least one of the plurality of components.

14. A method according to claim 13, wherein performing a factorization function further comprises performing a non-negative matrix factorization.

15. A method according to claim 13, wherein performing a factorization function further comprises performing an independent component analysis factorization.

16. A method according to claim 13, further comprising comparing the spectra of at least one of the plurality of components to a plurality of known spectra corresponding to a plurality of known components so as to screen the plurality of samples for a presence of the plurality of known components in the plurality of samples.

17. A method according to claim 12, wherein the determining step further comprises performing a correlation function for determining the characteristic value and wherein the characteristic value comprises a common spectra across the plurality of samples, the common spectra including a combination of at least a portion of the plurality of ions and corresponding to at least one of the plurality of components present in the plurality of samples.

18. A method according to claim 17, further comprising comparing the common spectra corresponding to a substantially pure component to a plurality of known spectra corresponding to a plurality of known components so as to screen the plurality of samples for a presence of the plurality of known components in the plurality of samples.

19. A method for analyzing data received from an analytical device across a plurality of samples, the method comprising:

automatically receiving, by a database, a data set, the data set being indicative of the presence of a plurality of ions in the samples, the data set including an elution time and an intensity corresponding to at least a portion of the plurality of ions across the plurality of samples;

correlating, by a processor device, the plurality of ions in the data set by the corresponding elution time to generate a data matrix corresponding to each of the plurality of samples at the elution time, the data matrix including a plurality of rows corresponding to each of the plurality of samples and a plurality of columns corresponding to the plurality of ions present in the respective samples; and performing, by the processor device, a factorization function on the data matrix for determining a characteristic value based at least in part on the intensity of the portion of the plurality of ions, the characteristic value corresponding to at least one of a plurality of components present in the plurality of samples, the components comprising at least two of the portion of the plurality of ions; and displaying, by a user interface, a visual indication of the characteristic value corresponding to at least one of the plurality of components across the plurality of samples.

\* \* \* \* \*